United States Patent [19]

Folden

[11] Patent Number: 5,527,272
[45] Date of Patent: Jun. 18, 1996

[54] BACTERIOCIDAL DIALYSIS COLLECTION BAG AND METHOD

[75] Inventor: Thomas I. Folden, Alamo, Calif.

[73] Assignee: Fresenius USA, Inc.

[21] Appl. No.: 196,973

[22] Filed: Feb. 14, 1994

[51] Int. Cl.$^6$ .................................................. A61M 37/00
[52] U.S. Cl. ..................... 604/4; 604/5; 588/258
[58] Field of Search ........................... 604/4, 5, 6, 892.1, 604/28, 29; 588/258; 424/424

[56] References Cited

U.S. PATENT DOCUMENTS

| | | | |
|---|---|---|---|
| 4,190,047 | 2/1980 | Jacobsen et al. | 604/28 |
| 4,372,313 | 2/1983 | Villari et al. | 604/327 |
| 4,417,892 | 11/1983 | Meisch | 604/323 |
| 4,529,398 | 7/1985 | Wong et al. | 604/49 |
| 4,923,598 | 5/1990 | Schal | 604/5 |

OTHER PUBLICATIONS

Hawley's Condensed Chemical Dictionary, Eleventh Edition, (1987), p. 628.

Primary Examiner—Paul B. Prebilic
Attorney, Agent, or Firm—Davis, Graham & Stubbs

[57] ABSTRACT

A method for manufacturing and using a dialysis collection bag, and the dialysis collection bag itself. A collection bag is fabricated with a sterilization tablet therein, having a soluble coating over a sterilization agent. When the collection bag is filled with used dialysis solution at the completion of the dialysis therapy, the soluble coating dissolves over a known period of time such as about 30 minutes. The delayed dissolution allows time to take a specimen sample of the unadulterated used dialysis solution. When the dissolution of the coating is completed, the tablet releases the sterilization agent to sterilize the used dialysis solution, so that pathogens are destroyed to prevent the transmission of disease in the event the collection bag is disposed of improperly.

7 Claims, 1 Drawing Sheet

BACTERIOCIDAL DIALYSIS COLLECTION BAG AND METHOD

FIELD OF THE INVENTION

The present invention relates to the field of medical dialysis including peritoneal dialysis and hemodialysis. In particular, the present invention relates to a dissolving bacteriocidal additive to a fluid collection bag to sterilize the fluid collected in the bag for safe disposal of the sterilized fluid.

BACKGROUND OF THE INVENTION

The common treatment for renal failure is hemodialysis treatment or peritoneal dialysis treatment. Both treatments utilize the diffusion of liquid through a semipermeable membrane. In the case of hemodialysis the membrane is in a dialyzer external to the patient, so that blood is withdrawn from the patient's vascular system and passed across the membrane while dialysis solution is passed across the other side of the membrane. Impurities in the blood are drawn through the membrane by osmotic pressure on the membrane and are disposed of in the discarded dialysis solution. In the case of peritoneal dialysis, the semipermeable membrane is the patient's peritoneal membrane. Dialysis solution is introduced into and retained for a period of time in the peritoneal cavity, and impurities in the blood migrate through the peritoneal membrane and into the dialysis solution. The dialysis solution with the impurities is then withdrawn from the peritoneal cavity and discarded into a "drain" bag or "collection" bag.

Both hemodialysis and peritoneal dialysis require significant amounts of dialysis solution, sometimes called dialysate. Common dialysates are primarily water, but with low ionic concentrations of dissolved sodium, potassium, calcium, magnesium, chloride, acetate, glucose and bicarbonate. The proportions of these and other compounds depends on a variety of factors. Regardless of the exact concentrations and relative proportions of the dissolved compounds, the main material in all dialysates is water.

Dialysis solutions have been premixed and prepackaged in a variety of mixes and sizes, so that the patient or the medical professional simply selects the desired size and mix of dialysate, makes the appropriate tubing connections to the prepackaged dialysates and to the patient and the dialysis machine, and then commences the procedure.

Regardless of the type of dialysis—peritoneal dialysis or hemodialysis—the procedure results in significant and sometimes substantial quantities of spent dialysis solution. This used dialysis solution has been exposed to and often contains a variety of pathogens including infectious diseases. There are cases in which used dialysis solution was found to contain viable HIV virus, for example, and there are undoubtedly other instances where used dialysis solution contained bacteria or viruses of other diseases as well.

This used dialysis solution is normally deemed "medical waste" and is required to be disposed of in accordance with applicable medical waste disposal procedures so as not to spread disease or contaminate water supplies. However, it is commonly recognized that the used dialysis solution is often disposed of improperly. Because many dialysis procedures are adapted for the convenience of home use, used dialysis solution is sometimes improperly discarded by simply putting it into trash receptacles for ordinary trash pick-up or pouring it into a sink or flushing it down the toilet. Even in hospitals and clinics, the high cost and inconvenience of medical waste disposal may tempt professionals to dispose of used dialysis solution improperly.

In the field of urinary catheters, there is a body of art pertaining to preventing pathogens from migrating from a urine collection bag up through a catheter and into the urethra. Such art is not directed toward the sterilization of the collected urine so that it can be properly disposed of without infecting others since urine does not normally contain infectious diseases even if from a diseased patient. Instead, this art is more directed toward preventing the collection bag from becoming a colonization site from which infection can migrate up the catheter to the patient himself. Illustrative of this urinary catheter art are U.S. Pat. Nos. 4,529,398 by Wong; 4,661,100 by Rechsteiner; 5,267,989 by Moyet-Ortiz; 4,863,445 by Mayhan; 4,417,892 by Meisch; and 4,372,313 by Villari.

The typical approach to preventing urinary tract infections in the urinary catheter prior art mentioned above is to include a sterilizing agent in the catheter or in the collection bag so that pathogens cannot migrate up the catheter. Such an approach is not appropriate for a dialysis collection bag, however, because in dialysis it is often desired to take specimen samples of the used dialysate. If the dialysate is sterilized upon entering the collection bag, then specimen samples cannot be cultured to test for live pathogens. It is also desirable in dialysis that the collection bag be entirely self-contained, so that the collection bag is manufactured with the sterilizing agent pre-placed within it to avoid a separate placement step at the time of use.

In the Wong patent, a dispensing device having a polymer with a chemoprophylactic agent is placed within the collection bag. The dispensing device begins sterilizing liquid in the collection bag immediately upon contact, and the device is designed such that the sterilizing properties continue for an extended period of time. In contrast, in dialysis collection bags it is desirable that the sterilization of the liquid not be commenced immediately upon contact with the dialysis collection bag, and in dialysis collection bags it is not necessary that the sterilization be contained for an extended period of time because the bag is filled in a very short period of time rather than over a period of many hours.

The Rechsteiner patent discloses a system with a urine collection bag having a fragile resinous material inside which is broken to release a sterilizing or diagnostic agent. The Rechsteiner patent is like the Wong patent in that it is designed for urinary catheter applications in which the collected urine must be sterilized immediately upon contact and over an extended period of time to prevent pathogen migration into the patient. The Mayhan patent is similar to the Rechsteiner patent, except that the resinous sterilizing agent is replaced with a slow-dissolving tablet. The Moyet-Ortiz patent discloses an antiseptic absorbent pad in a urine collection device; the Meisch patent discloses an outlet tube to a urine collection bag which is treated with a sterilizing agent to prevent pathogen colonization; the Villari patent discloses a urine collection bag with a tubular portion having a device for retaining an antimicrobial agent.

SUMMARY OF THE INVENTION

The present invention includes a dialysis collection bag and method of using the same in dialysis treatment and the disposal of used dialysis fluid. The apparatus of the invention includes a used dialysate collection bag having a sterilizing tablet within the collection bag. The sterilizing pill is coated with a gelatinous coating to delay the dissolution of the pill when the collection bag is filled.

The system is operated by performing peritoneal dialysis in the conventional manner, including the step of draining the used dialysis solution into the collection bag. The used dialysis solution begins to dissolve the gelatinous coating on the sterilization tablet immediately upon entering the collection bag. However, the gelatinous coating on the sterilization tablet is such that the tablet does not release the sterilization agent for about 30 minutes after the initial contact between the used dialysis solution and the sterilization tablet. This 30 minute delay allows time for a specimen sample to be taken from the collection bag before the sterilization agent is released to sterilize the used dialysis solution. Once the approximately 30 minutes expires so that the gelatinous coating is dissolved and the sterilization agent is released from the sterilization tablet, the sterilization agent is completely released, substantially immediately. Unlike in the case of urine collection bags used with urinary catheters, there is no need for slow and prolonged release over a period of time. The collection bag with sterilized used dialysis solution is disposed of in the standard proper manner as medical waste, but in the event that the disposal is improper for some reason, there is now much less likelihood of spreading infectious disease.

A variety of sterilization agents and gelatinous coatings are feasible for the sterilization tablet. In a preferred embodiment, the sterilization agent is calcium hypochlorite and the coating is sodium laurel sulfate.

DETAILED DESCRIPTION OF THE INVENTION

Figure 1:
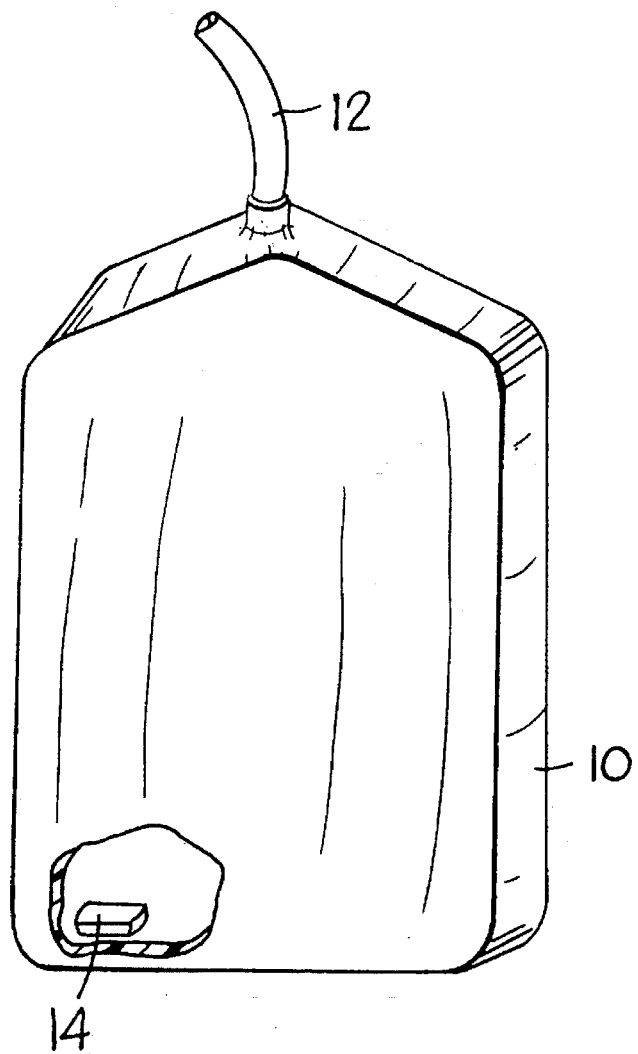
FIG. 1 shows a perspective view of a dialysis collection bag in accordance with the present invention

A perspective view of a dialysis collection bag in accordance with the present invention is shown in FIG. 1. A dialysis collection bag 10 is a bag-shaped element connected to a drain tube 12 which is connected to an ordinary peritoneal dialysis or hemodialysis tubing set (not shown). The collection bag 10 is sealed so that it is liquid tight and liquid cannot enter or leave it except through the drain tube 12. The collection bag 10 is constructed from plastic sheet material in the conventional manner known in the art and is sized appropriately so that the collection bag alone or in combination with a collection bag set has sufficient capacity to receive the used dialysis solution from a dialysis treatment.

Inside the collection bag is a sterilization tablet 14. The sterilization tablet 14 is preferably placed within the collection bag 10 at the time the collection bag is being manufactured. The sterilization tablet 14 is placed in the collection bag 10, and then the collection bag 10 is sealed to retain the sterilization tablet 14 therein. In a preferred embodiment, the tablet contains calcium hypochlorite. Other disinfectant agents are feasible as well, including lithium hypochlorite, sodium hypochlorite, and powder chloramines such as sodium p-toluene sulfonchloramide or other soluble disinfectants. The quantity and concentration of disinfectant should be sufficient to quickly disinfect 2–4 liters of used dialysis solution contained within the collection bag.

Figure 2:
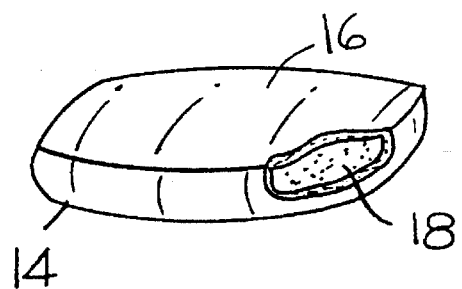
FIG. 2 shows a perspective, partial cut-away view of a sterilization tablet in accordance with the present invention.

An important aspect of the preferred embodiment of the invention is the use of a dissolving coating 16 over the body 18 of the sterilization tablet 14 as shown in FIG. 2. The coating must be dissolved by contact with the used dialysis solution before the disinfectant in the sterilization tablet 14 is released. As explained above, this delays the activation of the sterilization tablet 14 for a short time after initial contact with the used dialysis solution, to allow time to take a specimen sample before the disinfecting process commences. It has been found that the most convenient time period to provide between the initial contact between the sterilization tablet 14 and the used dialysis solution, to allow for the collection of a specimen sample, is about 30 minutes.

The coating 16 in the preferred embodiment is sodium laurel sulfate or gelatin. Other coatings are also feasible to provide appropriate delay in activation of the sterilization tablet 14, including ethylcellulose, hydroxypropyl-methylcellulose, titanium dioxide, sucrose stearate, hydroxypropylcellulose, polyvinylacetaldiethylaminoacetate, or acrylic latex sprays. The coating should dissolve in a pH range of 3–10.

The drain tube 12, as well as the rest of the tubing set and the collection bag 10 as well, may be sterilized at the time of manufacture by processes known in the art. Such processes include but are not limited to the use of ethylene oxide gas, steam, gamma rays and electron beams.

The manufacturing method will normally include the fabrication and assembly of the tubing set with its various elements such as valves, clamps and so on; the construction of the collection bag 10 with the sterilization tablet 14 therein; the attachment of the collection bag 10 to the drain tube 12; and the sterilization of the entire assembly by one or more of the known means mentioned above. The assembly is used in peritoneal dialysis and hemodialysis procedures much like tubing sets of the prior art. When the collection bag 10 is filled with used dialysis solution, the coating 16 to the sterilization tablet 14 begins to dissolve. The time it takes for the coating 16 to dissolve to the point where the sterilization agent is released may vary, as mentioned above, from a few seconds to an hour or longer. Preferably, the time is at least a few minutes, in order to allow time for a specimen sample to be taken, and the time is not so long that the used dialysis solution may be removed from the collection bag 10 prior to being sterilized by release of the sterilization agent. It has been found that about 30 minutes is ideal for this time period.

Once any desired specimen sample has been taken, and the coating 16 to the sterilization tablet 14 is dissolved so that the sterilization agent is released from the sterilization tablet 14 to sterilize the used dialysis solution, the collection bag 10 with the used, sterilized dialysis solution therein is discarded. It is still desirable that the collection bag 10 with the used, sterilized dialysis solution therein be discarded as medical waste, in accordance with proper medical waste disposal procedures. However, the prior sterilization of the used dialysis solution provides some assurance against the spread of disease in the event that such procedures are ignored or followed improperly.

What is claimed is:

1. A method of peritoneal dialysis, comprising: engaging with a dialysis patient a dialysis tubing set including a dialysis solution source and a collection bag having a sterilization device therein, wherein the sterilization device includes a sterilization tablet with a coating; performing the dialysis on the patient using the dialysis solution; draining the used dialysis solution into the collection bag; and sterilizing the used dialysis solution with the sterilization device in the collection bag by dissolving the coating with the used dialysis solution and releasing a sterilization agent from the sterilization device a known period of time after contact between the sterilization device and the used dialysis solution.

2. The method of claim 1, wherein the sterilization agent is a soluble disinfectant sterilizing the used dialysis solution is by a release of a sterilization agent from the sterilization device a known period of time after contact between the sterilization device and the used dialysis solution.

3. The method of claim 2, wherein the sterilization agent is selected from the group consisting of calcium hypochlorite, lithium hypochlorite, sodium hypochlorite and powder chloramines.

4. The method of claim 2, wherein the coating is selected from the group consisting of sodium laurel sulfate, gelatin, ethylcellulose, hydroxypropylmethylcellulose, titanium dioxide, sucrose stearate, hydroxypropylcellulose, polyvinylacetaldiethylaminoacetate and acrylic.

5. The method of claim 2, wherein the coating takes at least thirty minutes to dissolve.

6. A method of performing peritoneal dialysis on a patient, using a peritoneal dialysis solution, and safely disposing of the peritoneal dialysis solution, comprising: performing peritoneal dialysis on the patient using the peritoneal dialysis solution; draining the peritoneal dialysis solution into a collection bag having a sterilizing compound therein for sterilizing the used dialysis solution, wherein the sterilizing compound is coated with a coating that is soluble in the peritoneal dialysis solution; dissolving the compound coating with the peritoneal dialysis solution; sterilizing all the used peritoneal dialysis solution drained into the collection bag by contact of the peritoneal dialysis solution with the sterilizing compound; and discarding the sterilized peritoneal dialysis solution.

7. A method of performing peritoneal dialysis on a patient, using a peritoneal dialysis solution, sampling the peritoneal dialysis solution after performing peritoneal dialysis on the patient and safely disposing of the peritoneal dialysis solution, comprising: performing peritoneal dialysis on the patient using the peritoneal dialysis solution; draining the peritoneal dialysis solution into a collection bag having a sterilization compound therein coated with a coating that is soluble in the peritoneal dialysis solution; drawing a sample of peritoneal dialysis solution from the collection bag as the coating dissolves but before the coating is completely dissolved; sterilizing the peritoneal dialysis solution in the collection bag by contact with the sterilizing compound; and disposing of the sterilized peritoneal dialysis solution.

* * * * *